United States Patent [19]

Gravener

[11] Patent Number: 5,501,693
[45] Date of Patent: Mar. 26, 1996

[54] SURGICAL HEMOSTATIC CLIP

[75] Inventor: Roy D. Gravener, Fairfield, Conn.

[73] Assignee: United States Surgical Corporation, Norwalk, Conn.

[21] Appl. No.: 272,380

[22] Filed: Jul. 6, 1994

[51] Int. Cl.[6] .................................................. A61B 17/04
[52] U.S. Cl. ............................................ 606/157; 606/158
[58] Field of Search ........................... 606/151, 157–158, 606/142–143

[56] References Cited

U.S. PATENT DOCUMENTS

| | | |
|---|---|---|
| 3,006,344 | 10/1961 | Vogelfanger . |
| 3,175,556 | 3/1965 | Wood et al. . |
| 3,363,628 | 1/1968 | Wood . |
| 3,867,944 | 2/1975 | Samuels . |
| 3,874,042 | 4/1975 | Eddleman et al. . |
| 4,064,881 | 12/1977 | Meredith . |
| 4,146,130 | 3/1979 | Samuels et al. . |
| 4,188,953 | 2/1980 | Klieman et al. . |
| 4,278,091 | 7/1981 | Borzone . |
| 4,346,869 | 8/1982 | MacNeill . |
| 4,394,864 | 7/1983 | Sandhaus . |
| 4,407,286 | 10/1983 | Noiles et al. . |
| 4,412,539 | 11/1983 | Jarvik . |
| 4,414,721 | 11/1983 | Hufnagel . |
| 4,449,530 | 5/1984 | Bendel et al. . |
| 4,487,205 | 12/1984 | Di Gioranni et al. . |
| 4,489,875 | 12/1984 | Crawford et al. . |
| 4,519,392 | 5/1985 | Lingua . |
| 4,531,522 | 7/1985 | Bedi et al. . |
| 4,570,623 | 2/1986 | Ellison et al. . |
| 4,624,254 | 11/1986 | McGarry et al. . |
| 4,702,247 | 10/1987 | Blake, III et al. . |
| 4,796,627 | 1/1989 | Tucker . |
| 4,799,481 | 1/1989 | Transue et al. . |
| 4,844,066 | 7/1989 | Stein . |
| 4,971,198 | 11/1990 | Mericle . |
| 4,976,722 | 12/1990 | Faille . |
| 4,979,950 | 12/1990 | Transue et al. . |
| 5,171,250 | 12/1992 | Yoon . |
| 5,171,252 | 12/1992 | Friedland . |
| 5,171,253 | 12/1992 | Klieman . |
| 5,201,746 | 4/1993 | Shichman . |

FOREIGN PATENT DOCUMENTS

| | | |
|---|---|---|
| 853499 | 10/1952 | Germany . |
| 8522122 | 10/1985 | Germany . |

*Primary Examiner*—Gary Jackson

[57] ABSTRACT

A hemostatic clip is provided for application to body tissue which includes a clip body defining first and second opposed leg portions and a connecting bail portion. The leg portions each have an elongated tissue contacting surface defined thereon. The tissue contacting surface on the first leg portion has a longitudinally extending tongue formed thereon. The tissue contacting surface on the second leg portion has a longitudinally extending groove formed therein. The tongue and groove are asymmetrically disposed with respect to one another such that, upon approximation of the first and second leg portions, the tongue and groove cooperate in such a manner as to securely clamp body tissue therebetween.

12 Claims, 5 Drawing Sheets

SURGICAL HEMOSTATIC CLIP

BACKGROUND OF THE INVENTION

1. Field of the Invention

This invention relates to surgical clips, and more particularly, to hemostatic surgical clips for application to blood vessels or body tissue.

2. Description of Related Art

Ligation or occlusion of veins, arteries or blood vessels has been a necessary part of surgical procedures for many years. Typically, a severed vessel requires closure on both sides of a severance site before actual cutting takes place. In the past, surgeons used thread or suture material to tie a vessel prior to severing the vessel. This procedure was often time-consuming and required great dexterity on the part of the surgeon. In many instances, the assistance of a nurse or attending surgeon was necessary to perform this procedure.

The advent of surgical clips and clip appliers has greatly enhanced the art of vessel occlusion. Surgical clips are now commonly used for vessel ligation and occlusion. Examples of surgical hemostatic clips are described in U.S. Pat. Nos. 5,171,253; 5,171,252; 5,100,420; 5,084,057; 4,971,198; 4,844,066; 4,799,481; 4,702,247; 4,414,721; 4,188,953; 4,146,130; 3,867,944; and 3,363,628.

Many factors are critical to the design and performance of a surgical hemostatic clip. For example, the clip should not slip or become dislodged from a vessel after it has been applied. If the clip is not securely positioned, blood or other bodily fluid may begin flowing into the surgical site through the unclamped vessel. This serves to delay the operation while the surgeon locates and reclamps the vessel. Depending upon the type and location of the surgery, reclamping the vessel may be difficult.

Another consideration is that a surgical hemostatic clip should be designed to fully and completely close about a vein, artery, or vessel and completely stop the flow of blood or fluid therethrough. A clip which does not completely occlude the blood or fluid flow may be unsuitable for its intended function.

Generally, surgical hemostatic clips are U-shaped or V-shaped in configuration and define a pair of legs joined at one end by an apex or crown and spaced apart at the opposed ends to define an opening therebetween. The inside surfaces of the clip legs may be constructed in a manner to improve the occluding functions of the clip as well as to restrict dislocation of the clip after it has been applied to the target blood vessel. An example of a clip which purports to have such a construction is described in U.S. Pat. No. 4,976,722 to Failla. This clip includes an elongated groove in one of the legs thereof with a correspondingly configured tongue depending from the opposed leg thereof. Transverse grooves are formed across the tongue and groove.

An improved surgical hemostatic clip is needed however, to provide optimum vessel occlusion and clip retention on tissue during a surgical procedure.

SUMMARY

A hemostatic clip for application to body tissue is provided which includes a clip body defining first and second opposed leg portions and a connecting bail portion. The leg portions each have an elongated tissue contacting surface defined thereon. The tissue contacting surface on the first leg portion has a longitudinally extending tongue formed thereon and the tissue contacting surface on the second leg portion has a longitudinally extending groove formed therein. The tongue and groove are asymmetrically disposed with respect to one another such that upon approximation of the first and second leg portions of the clip, the tongue and groove interfit with one another to securely clamp body tissue therebetween.

In a preferred embodiment, a first axial centerline extends through the elongate tongue and a second axial centerline extends through the elongate groove. The second axial centerline is offset from the first axial centerline such that, upon approximation of the first and second leg portions of the clip, the tongue and groove cooperate in such a manner as to securely clamp body tissue therebetween.

In a further preferred embodiment, the tongue includes first and second opposed lateral facets and the groove includes first and second opposed lateral walls. The tongue and groove are oriented such that, upon approximation of the first and second leg portions of the clip, a greater gap distance exists between the first lateral facet of the tongue and the first lateral wall of the groove than exists between the second lateral facet of the tongue and the second lateral wall of the groove.

The unique orientation and construction of the tongue and groove of the various embodiments function to enhance the occlusive characteristics of the clip by generating lateral and torsional components of clamping force. Further features will become more readily apparent to those having ordinary skill in the art to which the claimed invention appertains from the following detailed description of the preferred embodiments of the invention taken in conjunction with the drawings.

BRIEF DESCRIPTION OF THE DRAWINGS

In order that those skilled in the art to which the claimed invention appertains may understand how to make and use the same, a detailed description of the construction thereof in accordance with preferred embodiment(s) will follow, referring by numerals to the accompanying drawings wherein:

DETAILED DESCRIPTION OF PREFERRED EMBODIMENTS

The surgical hemostatic clip of the subject invention is applied to body tissue by an appropriate surgical clip applying apparatus. A surgical clip applying apparatus generally has structure to position the clip relative to the tissue to which it will be applied, and a mechanism to deform the clip, usually by bending the clip at its apex so that the legs thereof clamp the tissue or vessel. Illustrative surgical instruments suitable for use in the application of the surgical hemostatic clips described herein are set forth in commonly assigned U.S. Pat. No. 4,509,518 to McGarry et al., and U.S. Pat. Nos. 5,084,057 and 5,100,420 to Green et al., the disclosures of which are herein incorporated by reference.

Figure 1:
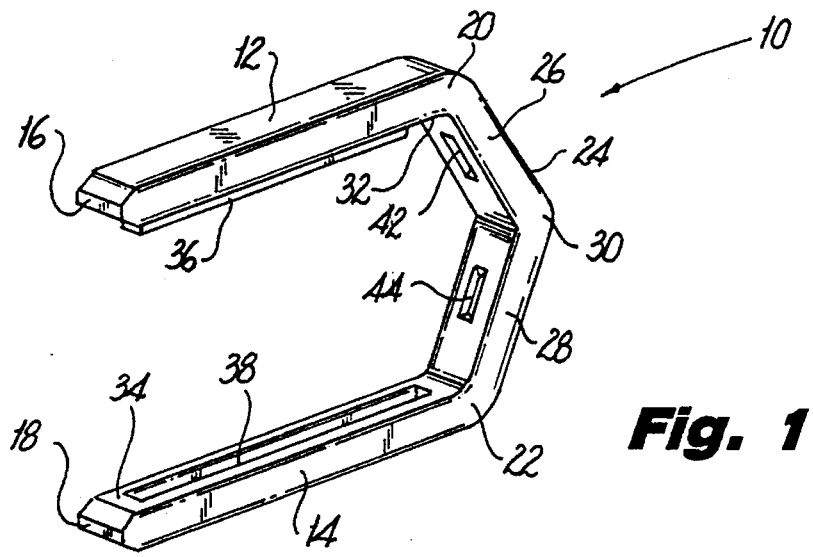
FIG. 1 is a perspective view of a surgical hemostatic clip constructed in accordance with a preferred embodiment.

Referring now to FIG. 1, surgical hemostatic clip 10 includes a pair of opposed leg portions 12 and 14 each having respective distal end regions 16 and 18, and respective proximal end regions 20 and 22. The proximal end regions 20 and 22 of each of the leg portions of hemostatic clip 10 are connected to respective ends of a bail portion 24. The bail portion 24 of hemostatic clip 10 is defined by angled bail sections 26 and 28 which culminate in an apex 30 to form the generally V-shaped configuration of hemostatic clip 10. Each of the leg portions 12 and 14 of hemostatic clip 10 define a respective tissue contacting surface between which tissue is clamped during application of the surgical hemostatic clip 10 thereto. In particular, leg portion 12 defines tissue contacting surface 32, while leg portion 14 defines tissue contacting surface 34.

Figure 2:
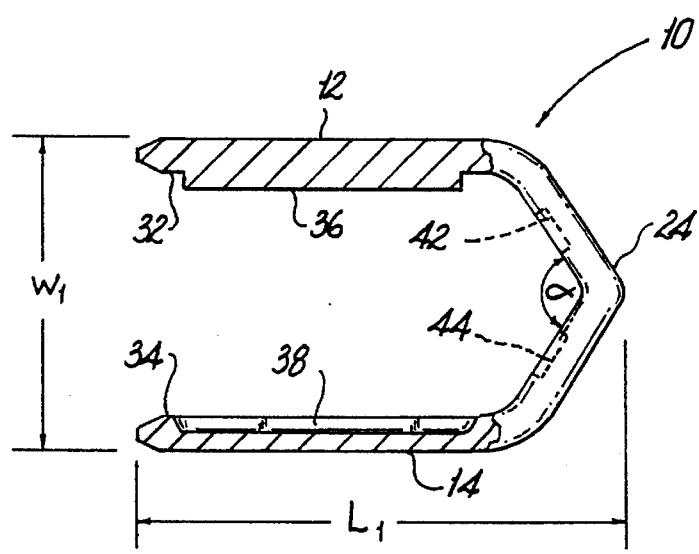
FIG. 2 is a side elevational view in partial cross-section of the surgical hemostatic clip of FIG. 1.
Figure 3:
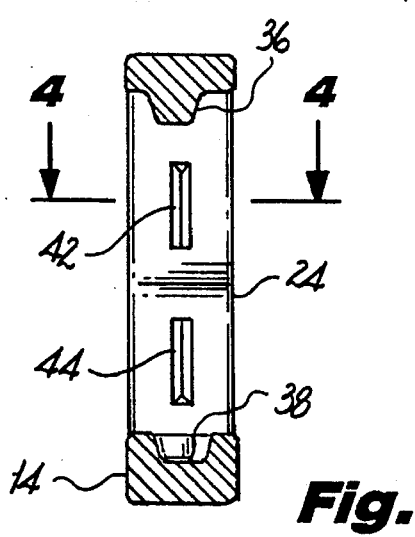
FIG. 3 is a front elevational view in partial cross-section of the surgical hemostatic clip of FIG. 1 illustrating the configuration of the tongue and groove structures provided on the opposed leg portions of the clip.
Figure 6:
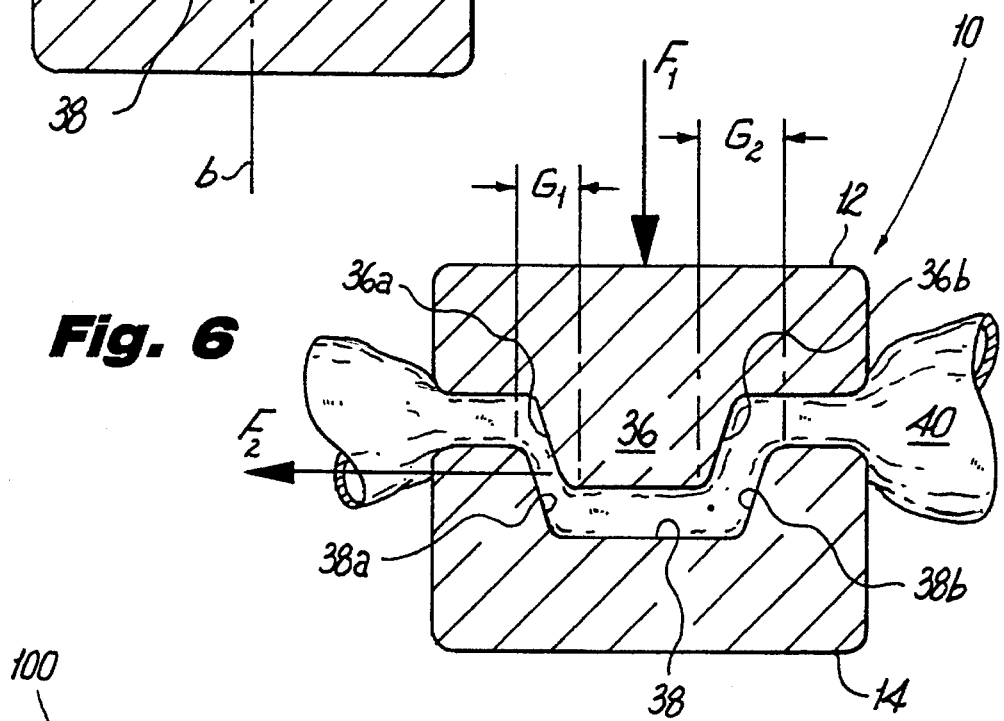
FIG. 6 is an enlarged cross-sectional view of the surgical hemostatic clip of FIG. 1 in a compressed state applied to a tubular vessel.

Referring to FIGS. 2 and 3, an elongate tongue 36 is formed on the tissue contacting surface 32 of leg portion 12, and an elongate groove 38 is formed in the tissue contacting surface 34 of leg portion 14. Elongate tongue 36 has a substantially trapezoidal cross-sectional configuration, and, as illustrated in FIG. 6, has opposed lateral facets 36a and 36b. Similarly, elongate groove 38 has a substantially trapezoidal cross-sectional configuration and opposed lateral walls 38a and 38b. Tongue 36 and groove 38 are oriented in such a manner as to provide a high degree of clamping force when applied to body tissue. In particular, the tongue 36 and groove 38 are asymmetrically disposed with respect to one another and, as a result, when leg portions 12 and 14 of clip 10 are approximated, a torsional component of clamping force is exerted by the clip legs on the clamped tissue. This torsional component of force will be greatest at a location proximate to bail portion 24.

Figure 5:
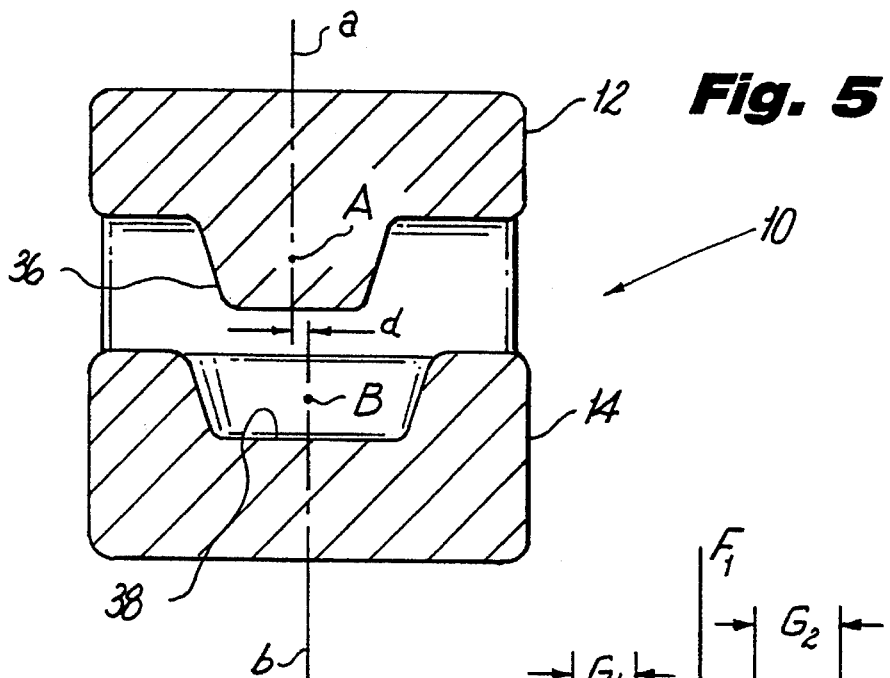
FIG. 5 is an enlarged cross-sectional view of the surgical hemostatic clip of FIG. 1 with the leg portions in a partially compressed position prior to application to a tubular vessel.

The asymmetric orientation of the tongue 36 and groove 38 is illustrated in FIG. 5. In particular, elongate tongue 36 defines an axial centerline "A" which intersects a transverse axis "a", and elongate groove 38 defines a similar axial centerline "B" which intersects a transverse axis "b". As best seen in FIG. 5, axial centerline "A" is laterally offset from axial centerline "B" a distance designated "d", resulting in the above-noted asymmetric orientation and related increase in clamping force.

The asymmetric orientation of tongue 36 and groove 38 has an additional effect on the clamping force exerted upon clamped body tissue. Referring to FIG. 6, when the opposed leg portions 12 and 14 of surgical clip 10 are approximated to clamp body tissue 40 therebetween, a normal clamping force $F_1$ is exerted on the tissue. At such a time, tongue 36 and groove 38 interfit in such a manner as to create a gap $G_1$ between lateral facet 36a and lateral wall 38a, and a gap $G_2$ is created between lateral facet 36b and lateral wall 38b. As shown in FIG. 6, gap $G_2$ is greater than gap $G_1$ and, as a result, the clamped tissue will have the effect of inducing a lateral component of force $F_2$ as the tissue attempts to equalize the two gap distances.

Figure 4:
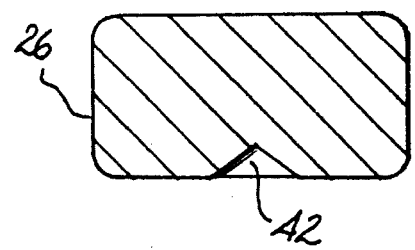
FIG. 4 is a cross-sectional view taken along line 4—4 of FIG. 3 illustrating the configuration of the tissue exudation ports formed in the bail portion of the clip.

Referring to FIGS. 3 and 4, a pair of tissue expansion notches 42 and 44 are defined respectively on the inner surfaces of the angled bail sections 26 and 28 of the bail portion 24 of hemostatic clip 10. As best seen in FIG. 4, expansion notches 42 and 44 have a substantially V-shaped cross-section which permits tissue exudation during the application of hemostatic clip 10 to tissue. The exudation of tissue into notches 42 and 44 further inhibits movement of the hemostatic clip 10 relative to the vessel to which it is applied.

With reference to FIG. 2, the surgical hemostatic clip 10 of the subject invention may be of any dimension suitable for application to vessels and body tissue. In one preferred embodiment, the length $L_1$ of the clip is about 0.3 inches and the width $W_1$ of the clip is from about 0.2 to about 0.25 inches. Furthermore, the angle alpha formed between the angled bail sections 26 and 28 of bail portion 24 is preferably from about 120° to about 140°. One having ordinary skill in the art to which the claimed invention appertains will recognize that other dimensions can also be used.

The tongue and groove structures described herein may be formed in clip 10 by fixturing the clip and applying an appropriate stamping force to the interior and exterior faces of leg portions 12 and 14. Alternatively, the tongue and groove structures may be formed by machining clip 10 or by other known metal or polymer processing techniques. For example, clip 10 may be molded with the tongue and groove structures formed therein. The surgical hemostatic clip may be fabricated from any biocompatible material including stainless steel, titanium, and tantalum, as well as plastic materials including nonabsorbable, bioabsorbable polymers, or combinations thereof.

Figure 7:
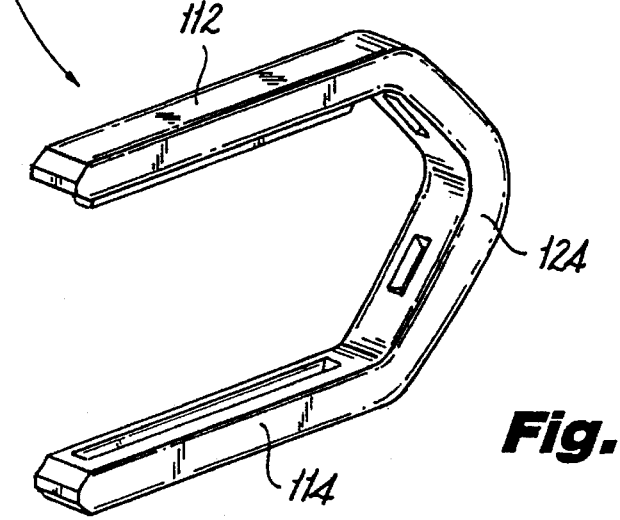
FIG. 7 is a perspective view of another surgical hemostatic clip constructed in accordance with a preferred embodiment which has a substantially U-shaped bail portion.

Turning to FIG. 7, another surgical hemostatic clip which is constructed in accordance with a preferred embodiment is illustrated and is designated generally by reference numeral 100. The construction of surgical hemostatic clip 100 is substantially similar to that of the surgical hemostatic clip 10 of the previous embodiment except that the opposed leg portions 112 and 114 thereof are connected by a substantially arcuate bail portion 124. Accordingly, surgical hemostatic clip 100 defines a substantially U-shaped configuration rather than the substantially V-shaped configuration of surgical hemostatic clip 10.

The clips described hereinabove may be fabricated in dimensions appropriate for the purposes mentioned herein and may be fabricated from any material suitable for use in surgical applications such as titanium, stainless steel, tantalum, or other metal alloys. Also useful are synthetic polymers, including bioabsorbable polymers.

Figure 8:
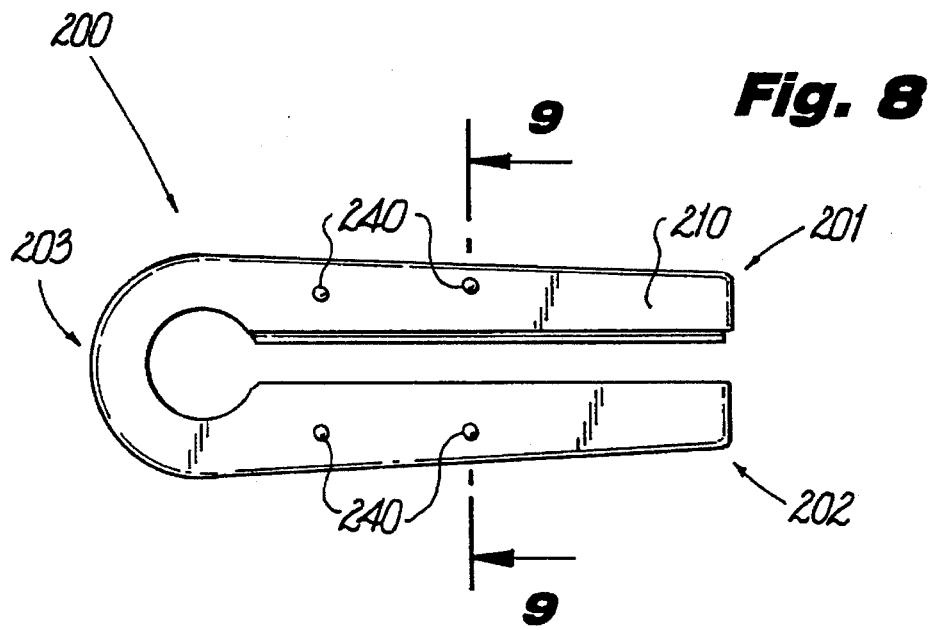
FIG. 8 is a side elevational view of an alternative embodiment of a hemostatic clip having a layered structure.
Figures 9, 10:
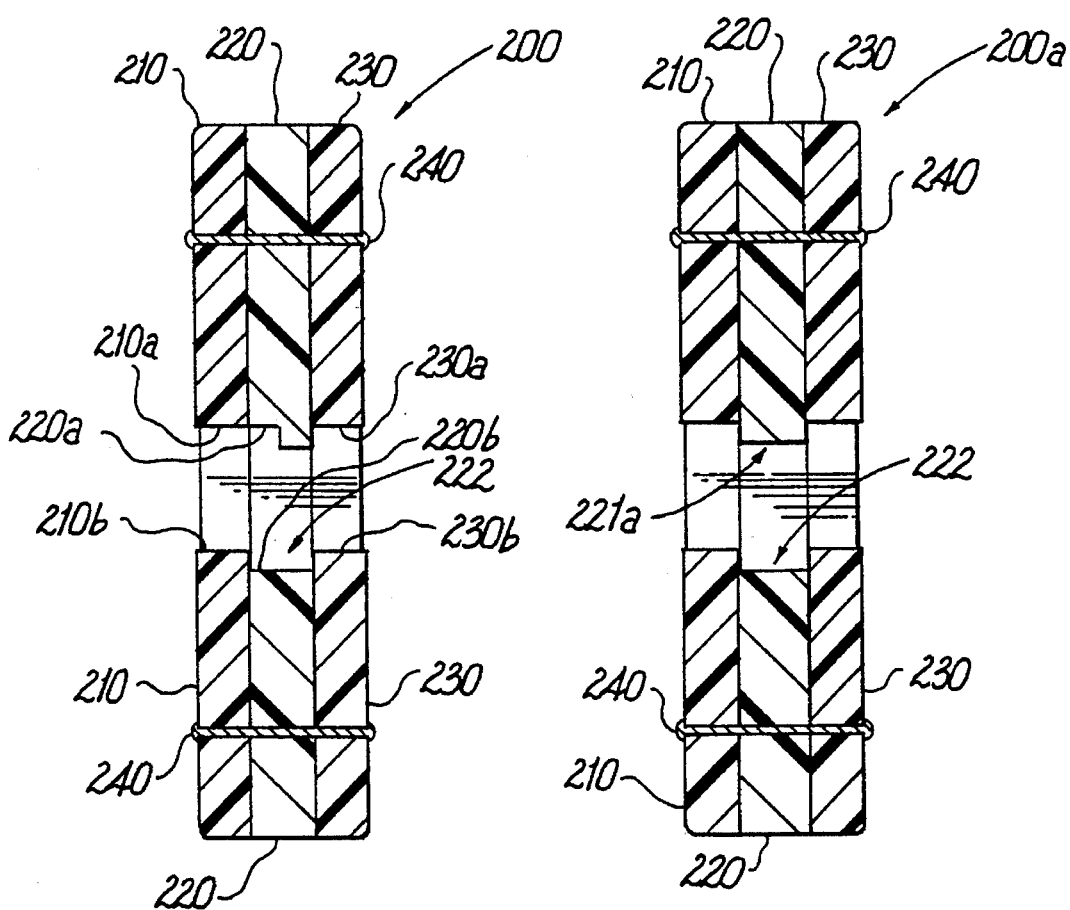
FIG. 9 is a sectional view of the layered hemostatic clip.
FIG. 10 is a sectional view of an alternative layered clip.

Referring now to FIGS. 8, 9 and 10, an alternative embodiment of the present invention is shown wherein hemostatic clip 200 is fabricated from three bonded layers 210, 220, and 230. Each layer comprises a sheet of polymeric material. The layers are bonded by conventional methods, such as adhesion, welding, etc., to form a laminate structure. The layers 210, 220, and 230 are preferably kept in alignment by means of alignment pins 240 disposed laterally through all of the layers. The layers are oriented such that each sheet 210, 220, and 230 comprises two leg portions 201 and 202 connected at a hinge portion 203. The layers may each be fabricated from the same polymeric materials. Alternatively, different polymeric materials may be used for one or more layers, i.e. the molecular structure of one of said sheets may differ from that of the other sheets. This difference of molecular structure may be in the form of chemical compositional difference or in the form of purely structural differences. For example, one sheet may be similar in composition to the other, but drawn or worked to increase crystallinity. Thus, one or two layers may be fabricated from a predominantly crystalline polymer while the remaining layer(s) may be fabricated from a predominantly amorphous polymer. The polymers may be bioabsorbable.

Each layer has opposing tissue contacting surfaces which are initially spaced apart to define a tissue receiving gap. Thus, layer 210 has tissue contacting surfaces 210a and 210b, layer 220 has tissue contacting surfaces 220a and 220b, and layer 230 has tissue contacting surfaces 230a and 230b. However, layer 220 is configured and dimensioned such that surface 220a defines a longitudinal projection 221 relative to tissue contacting surfaces 210a and 230a, and tissue contacting surface 220b defines a longitudinal recess 222, relative to surface 210b and 230b. The longitudinal centerline of projection 221 is preferably laterally offset from the longitudinal centerline of recess 222 such that when clip 200 is applied to body tissue and the legs 201 and 202 are closed, leg 201 will laterally shift so as to bring the longitudinal centerlines of projection 221 and recess 222 more closely into alignment. This adds a component $F_c$ to the clamping force on the tissue for a more secure grip.

Alternatively, as shown in FIG. 10, the layered structure of the clip may be constructed so as to create a projection 221a which, in embodiment 200a, does not result in a lateral shift since the longitudinal centerlines of projection 221a and recess 222 are initially in alignment.

Figure 11:
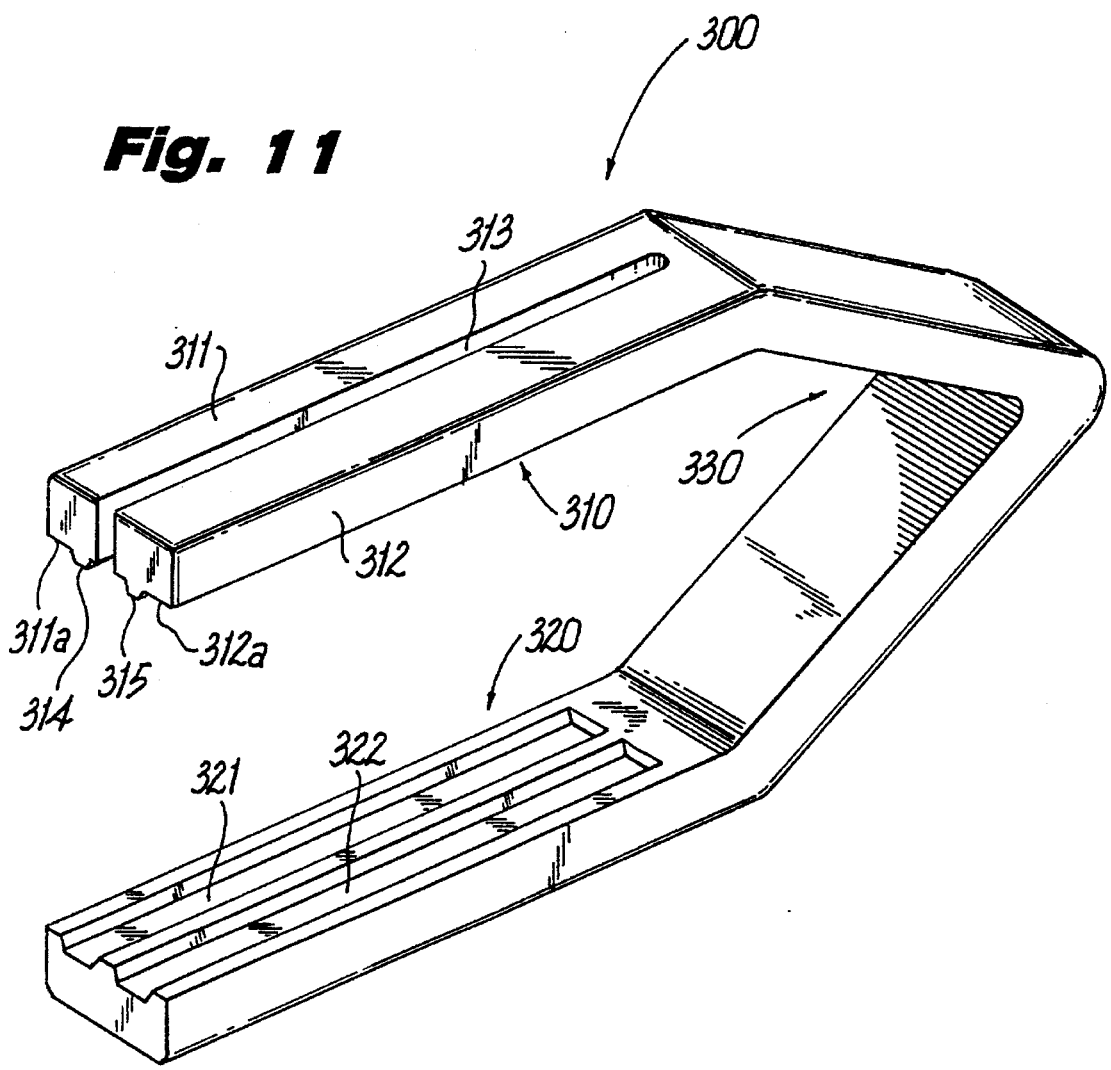
FIG. 11 is a perspective view if an alternative embodiment of a hemostatic clip with a slotted leg.

In yet another embodiment, the surgical clip may comprise two bendable prongs on the first leg. Referring to FIG. 11, clip 300 includes first and second substantially parallel leg portions 310 and 320 united at a U-shaped or V-shaped proximal bail end 330. The first leg portion 310 includes longitudinally extending prongs 311 and 312 separated by slot 313. Prong 311 includes on its tissue contacting surface 311a a longitudinally extending ridge 314. Prong 312 includes on its tissue contacting surface 312a, a longitudinally extending ridge 315. Leg portion 320 is not divided by a slot and includes two longitudinally extending recesses 321 and 322 which are configured and dimensioned to receive ridges 314 and 315, respectively. In the clip's initial configuration, the longitudinal centerlines of ridges 314 and 315 are offset from the respective longitudinal centerlines of ridges 321 and 322 in a direction towards the slot 313.

Figure 12:
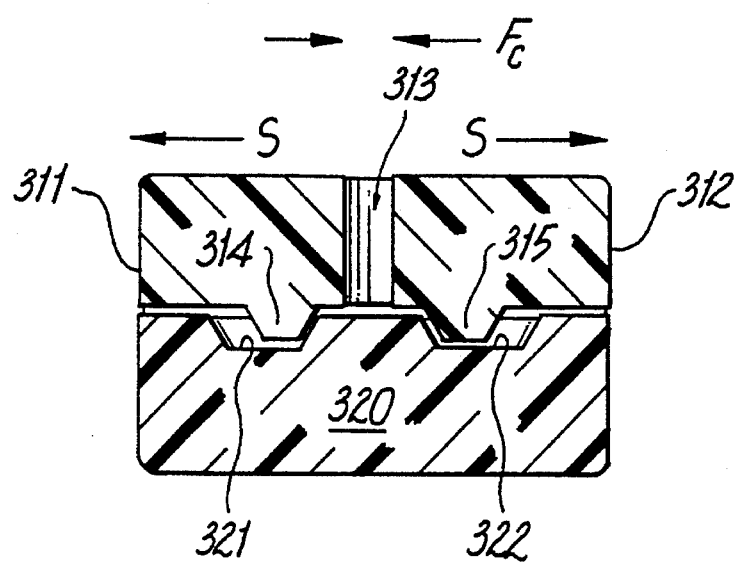
FIG. 12 is a sectional view of the clip of FIG. 11.

Referring to FIG. 12, when the clip is closed onto body tissue (not shown) positioned between the legs, the prongs 311 and 312 will have a tendency to resiliently splay in the direction S as shown in FIG. 9. This action sets up a corresponding lateral clamping counterforce as shown by arrows $F_c$.

Figure 13:
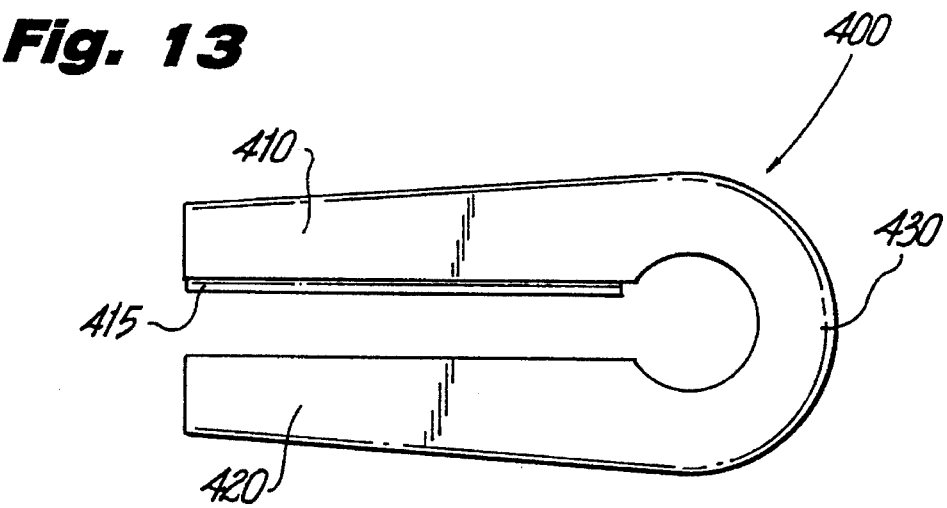
FIG. 13 is a side elevational view of an alternative embodiment of a multi-layerd clip.
Figure 14:
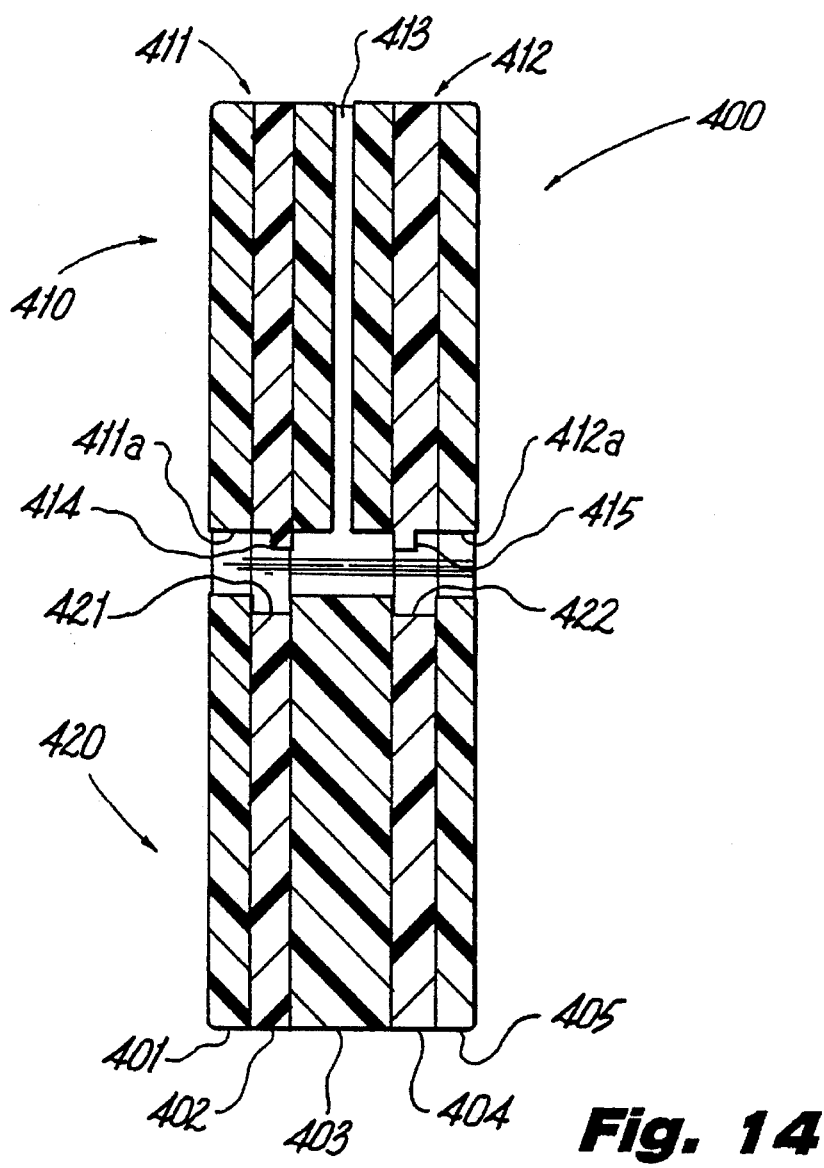
FIG. 14 is a sectional view of the multi-layered clip of FIG. 13.

The laminar structured clip may also be fabricated with a dividing slot in one leg. Referring to FIGS. 13 and 14, clip 400 is fabricated from layers 401, 402, 403, 404, and 405 of a synthetic polymeric material. The polymer is preferably bioabsorbable. Clip 400 includes first and second legs 410 and 420, respectively, connected by a proximal hinge portion 430. First leg 410 includes longitudinally extending prongs 411 and 412 separated by slot 413. Prong 411 includes on its tissue contacting surface 411a, a longitudinally extending ridge 414. Prong 412 includes on its tissue contacting surface 412a, a longitudinally extending ridge 415. Legs 420 includes two longitudinally extending recesses 421 and 422 which are configured and dimensioned to receive ridges 414 and 415, respectively. In the clip's initial configuration the longitudinal centerlines of ridges 414 and 415 are offset from the respective longitudinal centerlines of ridges 421 and 422 in a direction towards slot 414. When the clip 400 is applied to body tissue positioned between the legs, prongs 411 and 412 will have a tendency to splay outwardly, which sets up a lateral counterforce to facilitate clamping.

Although the hemostatic surgical clip has been described with respect to preferred embodiments thereof, it is apparent that changes or modifications made be made thereto without departing from the spirit or scope of the invention as defined by the appended claims.

What is claimed is:

1. A hemostatic clip for application to body tissue comprising:

a clip body defining first and second opposed leg portions and a connecting bail portion, each of the first and second opposed leg portions having an elongated tissue contacting surface defined thereon, the tissue contacting surface on the first leg portion having a longitudinally extending tongue formed thereon including first and second opposed lateral facets, the tissue contacting surface on the second leg portion having a longitudinally extending groove formed therein including first and second opposed lateral walls, the tongue and groove being oriented such that, upon approximation of the first and second leg portions, a greater gap distance exists between the first lateral facet of the tongue and the first lateral wall of the groove than exists between the second lateral facet of the tongue and the second lateral wall of the groove.

2. A hemostatic clip as recited in claim 1, wherein the tongue and groove have complementary trapezoidal cross-sectional configurations.

3. A hemostatic clip as recited in claim 1, further comprising means on an inner surface of the bail portion for permitting tissue exudation therein.

4. A hemostatic clip as recited in claim 3, wherein the means for permitting tissue exudation comprises a pair of spaced apart notches, each having a substantially V-shaped cross-sectional configuration.

5. A hemostatic clip as recited in claim 1, wherein the clip is fabricated from a material selected from the group consisting of stainless steel, tantalum, titanium, bioabsorbable polymers and nonabsorbable polymers.

6. A hemostatic clip as recited in claim 1, wherein the bail portion has a substantially U-shaped configuration.

7. A hemostatic clip as recited in claim 1, wherein the bail portion has a substantially V-shaped configuration.

8. The hemostatic clip of claim 1, wherein said clip body is fabricated from a plurality of polymer sheets bonded together to form a layered structure.

9. The hemostatic clip of claim 8, wherein said tissue contacting surfaces of said first and second leg portions are defined by edge surfaces of said polymer sheets.

10. The hemostatic clip of claim 8, wherein at least one of said plurality of polymer sheets differs in molecular structure from the other of said plurality of polymer sheets.

11. The hemostatic clip of claim 8, wherein at least one of said plurality of polymer sheets is fabricated from a synthetic bioabsorbable polymer.

12. The hemostatic clip of claim 11, wherein said synthetic bioabsorbable polymer is a polymer selected from the group consisting of glycolide, lactide, caprolactone, p-dioxanone, methylene carbonate, and chemical and physical combinations thereof.

\* \* \* \* \*